United States Patent
Benderev

(12) 
(10) Patent No.: US 6,436,029 B1
(45) Date of Patent: *Aug. 20, 2002

(54) EXTERNAL VIBRATORY EXERCISING DEVICE FOR PELVIC MUSCLES

(76) Inventor: Theodore V. Benderev, 26975 Magnolia Ct., Laguna Hills, CA (US) 92653

( * ) Notice: Subject to any disclaimer, the term of this patent is extended or adjusted under 35 U.S.C. 154(b) by 0 days.

This patent is subject to a terminal disclaimer.

(21) Appl. No.: 09/425,534

(22) Filed: Oct. 22, 1999

Related U.S. Application Data

(63) Continuation-in-part of application No. 09/078,937, filed on May 14, 1998, now Pat. No. 6,030,338, which is a continuation-in-part of application No. 08/558,642, filed on Nov. 13, 1995, now Pat. No. 5,782,745.

(51) Int. Cl.[7] .................................................. A61F 2/00
(52) U.S. Cl. ................................. 600/30; 128/DIG. 25; 128/885
(58) Field of Search ........................... 600/9–15, 29–32; 128/DIG. 25, 885

(56) References Cited

U.S. PATENT DOCUMENTS 6,030,338 A * 2/2000 Benderev ..................... 600/30
6,179,769 B1 * 1/2001 Ishikawa et al. ............. 600/15

* cited by examiner

*Primary Examiner*—John P. Lacyk
(74) *Attorney, Agent, or Firm*—Stetina Brunda Garred & Brucker

(57) ABSTRACT

A device and method for treating urinary as well as fecal incontinence by selectively and controllably imparting stimuli to the pelvic region. The device is adapted to be compressively positioned against the crotch of the user to thus identify target pelvic floor muscles and muscle groups responsible for urinary and/or fecal continence and provide periodic stimulus thereto by way of pressure, stretching, resistance, vibration, and/or heat. The frequency, duration, and extent of the stimulus may be varied as desired for exercise regimens. The device may further be utilized to impart magnetic therapy to the pelvic region of the user or may include a stimulator for imparting a pleasurable sensation to the sex organs. The device may additionally be utilized as a therapy for pain management.

16 Claims, 2 Drawing Sheets

EXTERNAL VIBRATORY EXERCISING DEVICE FOR PELVIC MUSCLES

CROSS-REFERENCE TO RELATED APPLICATIONS

The present application is a continuation-in-part of U.S. patent application Ser. No. 09/078,937 filed May 14, 1998 now U.S. Pat. No. 6,030,338 entitled EXTERNAL VIBRATORY EXERCISING DEVICE FOR PELVIC MUSCLES, which is a continuation-in-part of pending U.S. patent application Ser. No. 08/558,642 filed Nov. 13, 1995 now U.S. Pat. No. 5,702,795 entitled DEVICES AND METHODS FOR ASSESSMENT AND TREATMENT OF URINARY AND FECAL INCONTINENCE, and further relies on the disclosure made in Applicant's Disclosure Document, having a date of receipt of Jan. 16, 1998, Document No. not assigned.

STATEMENT RE: FEDERALLY SPONSORED RESEARCH/DEVELOPMENT (Not Applicable)

BACKGROUND OF THE INVENTION

Urinary incontinence is believed to affect 15% to 30% of noninstitutionalized persons over the age of 60, and more then 50% of elderly persons (over the age of 60) who reside in nursing homes.

The presently available modes of treatment for urinary incontinence fall into four general categories, namely: i) management apparatus, ii) behavioral, iii) pharmacologic, and iv) surgical.

i. Management Apparatus For Incontinence

The management apparatus modes of treatment generally comprise absorbent and/or catheter structures worn by a user to retain any urinary and/or fecal incontinence. In their simplest forms, such devices comprise diaper-like structures which must be periodically changed by the user. Although such management apparatus has proven generally effective in masking the results of incontinence, they are uncomfortable to wear, difficult to change, and oftentimes fail during use thereby embarrassing the user.

ii. Behavioral Treatment For Incontinence

The use of behavioral training as a treatment for urinary and/or fecal incontinence can involve numerous behavioral techniques including; bladder retraining (e.g., voiding on a timed schedule), and/or the performance of exercises (e.g., Kegel exercises) to strengthen and retrain a group of muscles collectively known as the "pelvic floor muscles." As an adjunct to these behavioral training techniques, various intravaginal and/or intra-anal devices may be utilized to facilitate the performance of such pelvic muscle training exercises. Such intravaginal and/or intra-anal devices have included weighted apparatus such as intravaginal cones. Exemplary of such prior art include weighted cone devices such as the "FEMINA" cone manufactured by Dacomed Corporation, 1701 East 79th Street, Minneapolis, Minn., 55425. Other types of prior art devices include electromyographic (EMG) transducers or sensors which are insertable into or placed just outside of the vagina and/or anus to obtain EMG data indicative of baseline pelvic floor muscle tone and/or contraction(s) of the pelvic floor muscles during the performance of specific muscle contraction exercises. Such EMG data may be usable for diagnostic purposes as well as for monitoring the performance and/or effect of muscle training exercises. Some EMG devices have included means for providing visual or auditory feedback to assist the patient in the performance of pelvic floor muscle exercises (e.g., Myoexorciser III, available from Verimed 1401 East Broward Boulevard, Suite 200, Fort Lauderdale, Fla. 33301 and the PRS 8900 Office System made by Incare Medical Products, Libertyville, Ill. 60048.

Additionally, the prior art has included at least one transvaginal electrical stimulation device which is operative to deliver periodic or timed electrical stimulation to the pelvic floor muscles and nerves. Such electrical stimulation causes involuntary contraction of the pelvic floor muscles and may serve as an adjunct to the performance of volitional exercise and/or other behavioral training techniques (e.g., Microgyn II Stimulation Device, InCare Medical Products, Division of Hollister Incorporated, 2000 Hollister Drive, LibertyVille, Ill., 60048 and also the Innova Feminine Incontinence Treatment System available from EMPI, Inc., 1275 Grey Fox Road, St. Paul, Minn. 55112).

Although some of or all of the above-described devices and systems for exercise and/or training of the pelvic floor muscles may be effective in the treatment of urinary incontinence, there remains a need for the development of improved devices and systems which are capable of strengthening and training the pelvic floor muscles in minimal time, with minimal assistance from physicians or other health care professionals as well as a system which serves to remind a user to perform muscle exercises and to provide proprioceptive input to assist the user in exercising and strengthening desired muscles.

iii. Pharmacologic Treatment For Incontinence

The prior art pharmacologic treatment of urinary incontinence typically involves the long term administration of drugs. Such pharmacologic treatment may result in drug-related side effects. Also, the efficacy of such pharmacologic treatment is frequently limited and largely dependant upon the patient's ability or willingness to comply with the prescribed drug dosage schedule.

iv. Surgical Treatment For Incontinence

The prior art surgical modes of treatment of urinary incontinence typically involves the performance of one or more major surgical procedures under anesthesia. These major surgical procedures can be associated with significant risks and may sometimes result in post-surgical failure, infections, or other complications. Also, these surgical procedures typically result in significant expense to the patient and/or the patient's third party insurer.

As such, there exists a substantial need in the art for an incontinence treatment system and methodology which reduces or eliminates the need for prior art management apparatus and/or surgical, treatments, reduces the use of long-term drug administration, accentuates muscle strengthening and training while reminding a patient to conduct muscle strengthening exercise, as well as provide a proprioceptive input to assist the patient in contracting the appropriate muscles and/or muscle groups necessary for the effective treatment of incontinence.

In addition to the need for an incontinence treatment system as discussed above, there is a further need in the art for a system that can further promote genitourinary health. In this respect, and separate and apart from the treatment of incontinence, there is currently lacking any apparatus or system that is known to facilitate genitourinary health via the deployment of a variety of therapeutic modalities, and in particular magnetic therapy and vibratory stimulation.

With respect to the former, it is well-known in the art to use magnets to therapeutically relieve pain and discomfort. In this regard, the use of magnets is reportedly successful in treating a wide variety of conditions, including arthritis, rheumatism, fibromyalgia, back pain, headaches, muscle strains and sprains, joint pain, tendinitis and shoulder pain, among many others.

To produce the desired therapeutic benefit, it is presently believed that exposure to bio-magnetic negative poles, or north-poles, has the ability to relieve pain, reduce swelling, promote tissue alkalinization, and increase tissue oxygenation. Exposure to south or positive-poles, in contrast, is believed to increase swelling, promote anxiety and other adverse side-effects. As such, current magnetic therapy dictates surrounding all or a portion of the body in close proximity to the north or negative-poles of a plurality of magnets.

To date, however, there is currently lacking any type of apparatus or system for deploying magnetic therapy to the pelvic region of an individual such that the muscles, organs and anatomic structures in and around such area, such as the small and large intestines, rectum, lower urinary tract, sexual or reproductive organs, hip/lower back and other neighboring joints or bones, can receive the benefits thereby. While new medical devices, and in particular the NebControl™ Pelvic Floor Therapy System, produced by Neotonus, Inc., 810A Franklin Court, Marietta, Ga., 30067, USA, are now available which impart pulses of magnetic fields to the pelvic floor to treat incontinence, such apparatus and method utilize a sophisticated and expensive therapy chair. Such therapy chair produces and directs strong pulse magnetic fields of sufficient magnitude to cause nerve impulses situated in the pelvic floor, which innervate the muscles responsible for continence. The fields pass through the targeted treatment area to deliver the therapeutic action. Unfortunately, such device, in addition to being costly, further requires medical supervision and the deployment of medical equipment that must necessarily be maintained at a medical facility.

With respect to vibratory stimulation as a means for promoting genitourinary health, it is well-known that the same can increase blood flow to the genitourinary region and can improve sexual well-being via stimulation of the sexual organs. Presently lacking in the art though, is a system or apparatus for imparting perceptible input to the sexual/reproductive organs in the form of vibratory stimulation that, in addition to applications for treating incontinence, can further serve to stimulate and create feelings of sexual well-being and gratification. In this regard, there is specifically lacking in the art any type of system or apparatus that can be selectively controlled to impart a degree of stimulation of sufficient magnitude and for sufficient duration to induce orgasm.

There is likewise lacking in the art any type of device for imparting cutaneous stimulation to the pelvic region as a means of pain management. In this respect, there is presently not available any type of apparatus or system that selectively imparts stimulus to the pelvic region of a patient which, in turn, can substantially decrease or inhibit the transmission of impulses from small diameter afferent peripheral nerve fibers to the spinal cord cells to thus modulate pain transmission. In this regard, there is lacking any type of system that generates cutaneous stimuli that is specifically applied to the pelvic region to illicit activity from large-diameter afferent nerve fibers to consequently inhibit transmission of nociceptive signals generated by excitatory activity in small-diameter fibers converging in the superficial laminae of the spinal cord dorsal horn (i.e., the substantia gelatinosa) consistent with the gate-control theory of pain.

BRIEF SUMMARY OF THE INVENTION

In accordance with the present invention, there is provided an external exercising signaling device which is positionable upon the crotch of a patient to identify target muscle groups responsible for fecal and/or urinary continence, and provide a signal to the patient to perform the appropriate muscle strengthening exercises therefor. According to a preferred embodiment, the device comprises a saddle member having a signaling device housed therein, the latter being designed and configured to impart a perceptible stimulus against a portion of the crotch of the individual upon which the saddle member is positioned to thus remind the patient to perform the desired pelvic muscles strengthening exercises.

The signaling device may preferably comprise a pressure-exerting device, heater, or any other like device capable of generating a perceptible stimulus. In an alternative preferred embodiment, the signaling device may comprise a stimulator that is configured to impart stimulation to the sexual organs to improve sexual well-being through pleasure, as part of its ability to generate a perceptible stimulus. A powersource, i.e., a battery, coupled to the signaling device and preferably housed within the saddle member is provided to drive the signaling device. Additionally, a timer apparatus may be mounted on or within the device to trigger and control the timing, duration, repetitions, and frequency of perceptible stimulus signals generated by the signaling device on a predetermined time schedule.

Still further in accordance with the invention, a remote controlled triggering device may be used in addition to, or in place of, a timer or other control apparatus mounted or housed within the saddle member. Such remote control apparatus may be utilized to trigger, control and/or schedule all operational parameters of stimulus produced by the signaling device from a remote location.

In addition, or as an alternative to treating urinary incontinence, the present invention may further be utilized to impart magnetic therapy to the pelvic/genitourinary region of an individual. In this regard, the saddle member may be provided with one or more magnetic elements positioned therewith or thereupon such that the negative or north pole thereof is situation in close proximity to the pelvic/genitourinary regions of the body for prolonged periods of time.

The present invention can additionally be utilized for pain management by generating a cutaneous stimuli to modulate the transmission of pain. In this regard, the exercise-stimulation device of the present invention is adaptable to impart stimuli to the nerves of the pelvic floor which, as a consequence, can selectively and substantially diminish nociceptive neural transmissions.

Still further in accordance with the invention, there is provided a method of treating urinary and/or fecal incontinence in a patient. In general, the method comprises the steps of compressively positioning an external exercising device of the forgoing character upon the crotch of a patient, and utilizing the device to intermittently deliver stretch, resistance, vibration, pressure or heat stimuli against the crotch and/or adjacent muscles thereabout to facilitate the performance of pelvic muscle strengthening exercises by the patient upon whom the device is positioned.

There is likewise provided a method of managing pain in a patient. Such method preferably comprises the steps of compressively positioning the external stimulation device discussed above and utilizing the device to impart a cutaneous stimulus of sufficient nature to the pelvic region to modulate pain transmission by inhibiting nociceptive neural transmissions.

BRIEF DESCRIPTION OF THE DRAWINGS

These, as well as other features of the present invention, will become more apparent upon reference to the drawings, wherein.

DETAILED DESCRIPTION OF THE PREFERRED EMBODIMENTS

The following detailed description and the accompanying drawings are provided for the purpose of describing certain presently preferred embodiments of the invention only, and are not intended to limit the scope of the claimed invention in any way.

Figure 1:
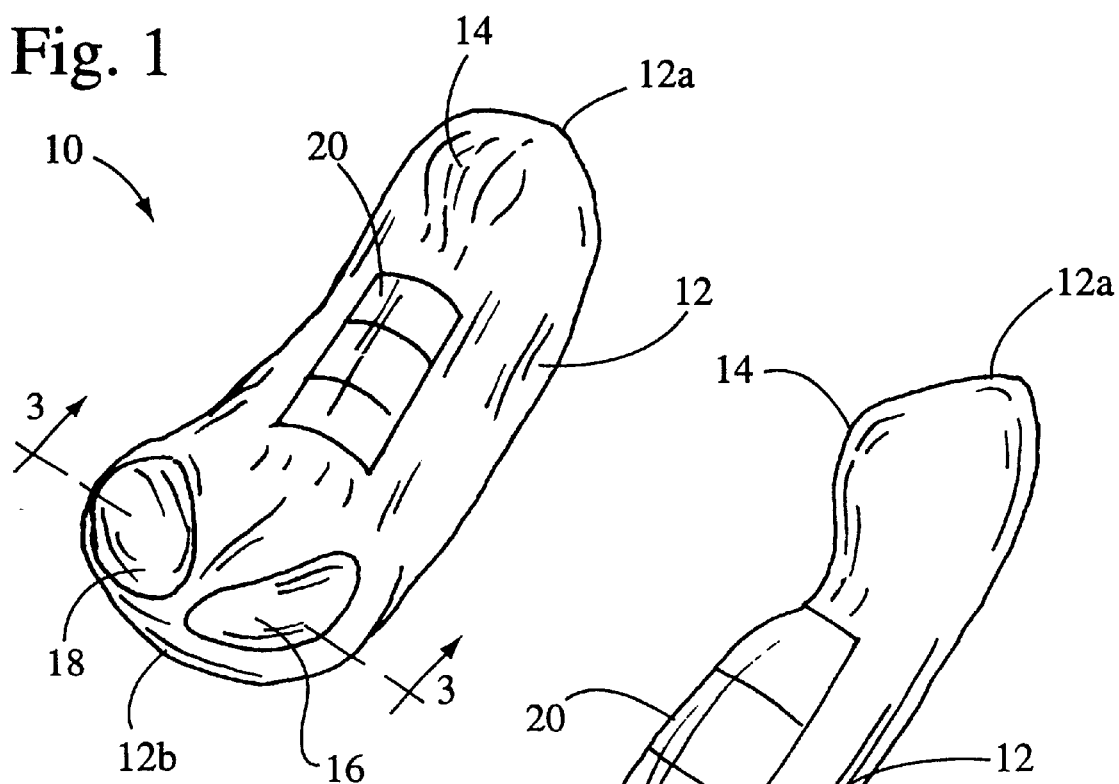
FIG. 1 is a perspective view of an external exercising device for facilitating the pelvic muscle strengthening exercises constructed in accordance to a preferred embodiment of the present invention.

Referring now to the drawings, and initially to FIG. 1, there is shown an external exercise device 10 constructed according to a preferred embodiment of the present invention. The device 10 is specifically designed to be utilized for the effective treatment of both urinary and fecal incontinence in females as well as male users or patients similar to those disclosed in pending parent application Ser. No. 08/558,642, the teachings of which are expressly incorporated herein by reference. The device 10 is additionally effective imparting magnetic therapy to the pelvic and genitourinary regions of the body, as well as imparting a pleasurable vibratory stimulation of the sexual organs to improve sexual well-being. The device 10 may further be utilized in pain management.

Figure 3:
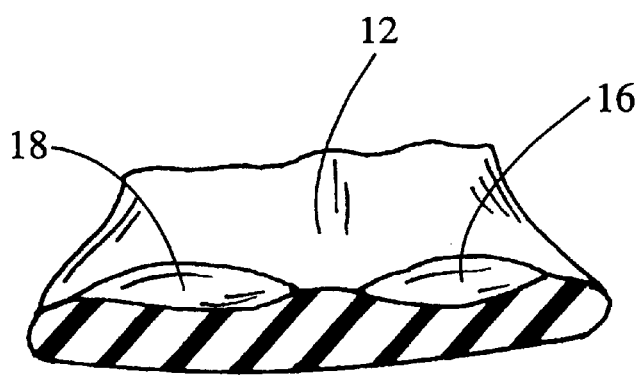
FIG. 3 is a cross-sectional view taken along the line 3—3 of FIG. 1.

As shown, the device 10 comprises an elongate saddle member 12 having an anterior end 12a and a posterior end 12b that is designed and configured to be compressively positioned (i.e., straddled) against the crotch of the user or patient. To accommodate and complement the anatomy of human beings, there is formed a cushioning member 14 upon the anterior end 12a of the saddle member 12, and a pair of opposed, generally oval-shaped recesses 16, 18 formed upon the posterior end 12b of the saddle member 12, the latter being more clearly depicted in FIG. 3.

Figure 4:
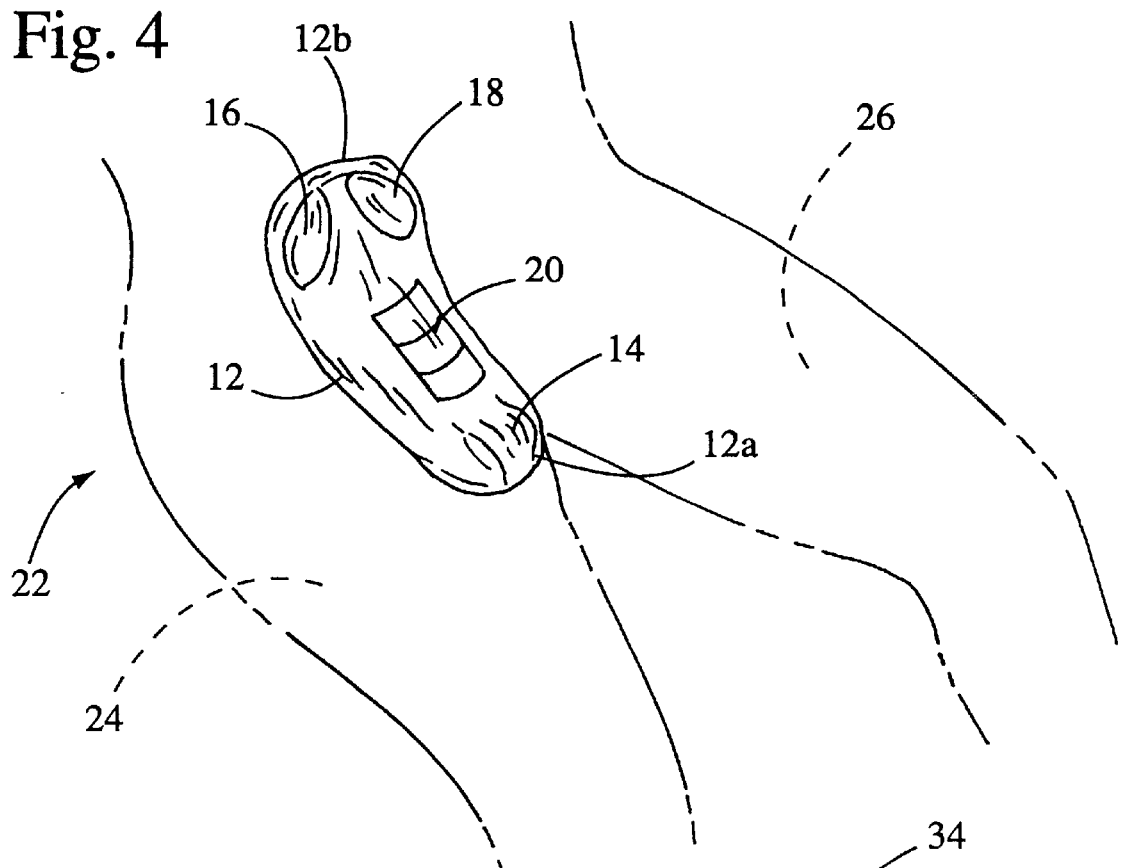
FIG. 4 is a perspective view of the device depicted in FIG. 1 as aligned with and positioned upon the crotch of a patient, the latter is shown in phantom.

As will be appreciated by those skilled in the art, cushion member 14 and recesses 16, 18 enable the saddle member 12 to adapt to the contours of the crotch between the respective inner thighs 24, 26 of the user or patient 22, as depicted in FIG. 4. In this regard, cushioning member 14 and recessed portions, 16, 18 are specifically designed and adapted to accommodate the user's skeletal structure of the pelvis when the patient is straddling the same in either a standing or sitting position. The saddle member 12 may likewise be designed and adapted to conform about and/or envelop the sexual organs to impart a pleasurable stimulus thereto.

It will be further recognized and appreciated by those skilled in the art that the saddle member 12 may likewise take a variety of shapes and forms. The saddle member may further be preferably provided with selectively sized and positioned cushioned members that can serve to selectively apply pressure to various pressure points around the pelvic region. In this regard, it is contemplated that the saddle member 12 may itself be utilized to impart acupressure-type therapy by applying pressure via specific contours formed on the saddle member 12 at specific points upon the pelvic and genitourinary regions known in the art to relieve pain and possibly treat certain illnesses.

Figure 2:
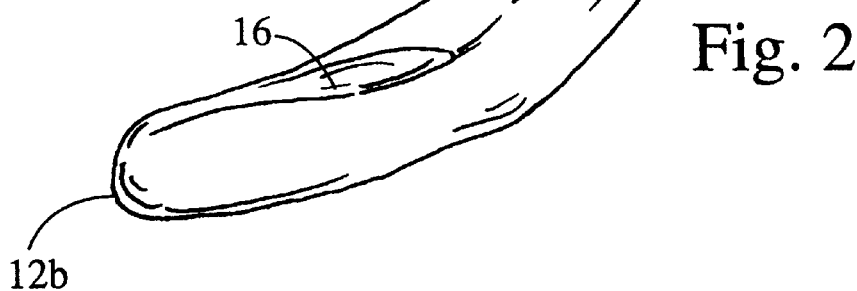
FIG. 2 is a side view of the device depicted in FIG. 1.

Housed within the saddle member 12 is a signaling device 20. As illustrated, the signaling device 20 is selectively positioned within the saddle member 12 such that a portion thereof is maintained in an upwardly-oriented configuration, as shown is FIG. 2, so that in use the stimuli generated thereby can be easily and directly perceived by the user/patient. Specifically, the signaling device 20 will be configured to impart perceptible stimulus to one or more of the pelvic muscles, including but not limited to, the levator ani, obturator internus, sphincter, bulbospogeosus buobocavernus, transverse perineal, and/or ischiocavernus. The signaling device 20 may be further designed and oriented to impart a stimulus to the specified pelvic muscles, but may further impart a stimulus one or more of the muscles adjacent to the pelvis, including the adductor longus, external hip rotators, and/or the gluteal muscles.

The signaling device 20 is operative to provide timed or periodic changes in stimuli such as pressure, heat, and/or vibration to thus identify the aforementioned target pelvic muscles/muscle groups responsible for fecal and/or urinary continence and promote proprioceptive neuromuscular facilitation and serve as a reminder to perform, and/or will facilitate the performance of, the appropriate muscle-strengthening exercises (e.g., Kegal exercises) by the patient upon whom the external exercise device 10 is positioned. A more detailed description of proprioceptive neuromuscular facilitation is found in Sullivan, P. E., et al.: "An Integrated Approach To Therapeutic Exercise", published by Reston Publishing Co., Reston, Va., pages 161–183, the disclosure of which is expressly incorporated herein by reference.

To enable the signaling device 20 to impart the stimulus to the patient to identify the target muscles and remind the patient to perform the pelvic muscle strengthening exercises therefor, a battery or powersource (not shown) is provided that is preferably housed within the saddle member 12. Additionally, a small triggering and control apparatus, such as the timer (not shown), may likewise be disposed within the saddle member 12 and connected to the signaling device 20 to cause the same to impart a stimulus to the patient on a predetermined time schedule. Alternatively, a remote control or telemetric switch or signal may be utilized to receive remote control signals and to schedule the operation of the device by actuating or de-actuating the signal device 20, as desired. By virtue of the stimulus produced by the signaling device 20, the patient will sense the vibration, heat and/or exertion of pressure, stretch or resistance against a portion of the perineum, vaginal, and/or anal wall and/or adjacent muscles thus identifying the target muscles or muscle groups sought to be strengthened. The patient will be thereby reminded and compelled to volitionally perform the prescribed pelvic floor muscle exercises. With respect to the incorporation of a pressure exerting mechanism, the pressure, stretch and/or resistance thereby created will thus improve the muscle-strengthening efficacy of such exercises by proprioceptive neuromuscular facilitation. After a predetermined time (e.g., sufficient time for the patient to perform the prescribed muscle exercise) has expired, or upon delivery of other triggering input (e.g., a remote control signal), the stimulus provided by the signaling device 20 is selectively terminated, i.e., the signaling device 20 is caused to assume a rest or non-operational mode.

After the signaling device 20 has returned to such "non-operative" mode, the device 10 may remain in such mode and continuously compressively engaged against the user's crotch, as depicted in FIG. 4. Upon expiration of a predetermined time period or upon receipt of a triggering input signal, the signaling device 20 will become actuated to thus assume its "operative" mode, whereby the device 10 will return to its stimulus-producing mode for an additional period of time.

The above-described sequence of events may be repeated on any prescribed schedule, or at any prescribed frequency or variable extension, so long as the device 10 remains sufficiently compressed against the patient. The patient will be thereby reminded and compelled to volitionally perform the prescribed pelvic wall muscle exercises of the identified pelvic floor muscles. Also, the vibration, heat, pressure, stretch and/or resistance created by the operatively positioned signaling device 20 will improve the muscle-strengthening efficacy of such exercises by proprioceptive neuromuscular facilitation.

In a more highly preferred embodiment, the signaling device comprises an enhanced stimulator mechanism that is selectively positionable against the sexual organs such as the testicles and/or penis of the male and/or the clitoris and labia of the female, such that pleasurable stimulation may be imparted thereto. Along these lines, it is contemplated that such stimulator mechanism, which may take any of a variety of those known in the art, can be adapted to selectively and controllably pulsate in a desired manner against a specified area, such as the clitoris or labia, to enable the user to experience a gratifying, pleasurable sensation, including orgasm, to thus improve and promote the user's sexual well-being. Moreover, it is contemplated that the stimulator mechanism may be specifically configured to impart a desired degree of friction, heat, suction and the like, as well as be specifically contoured to compressively engage against sexual organs so that the same may be utilized in a variety of sexual practices, including but not limited to, interactive sexual practices.

As will be understood by those skilled in the art, as an alternative to transitioning between operative and non-operative modes whereby a stimulus is produced by the signaling device stimulator 20 at predetermined times, such device 20 may operate in a reverse manner whereby the device 20 is maintained in a continuously operative mode such that a first stimulus is continuously produced thereby. At predetermined times, such stimulus may be either increased or decreased to a degree such that the patient is provided with a perceptible change in the stimulus produced by the signaling device 20, which consequently serves to remind the patient to perform the prescribed pelvic floor muscle exercises and/or impart a desired degree of pleasurable sensation.

As will further be appreciated by those skilled in the art, the signaling device 20 may be operative to impart a specified cutaneous stimuli sufficient to modulate pain transmission in pain management procedures in accordance with the gate-control theory of pain. Pursuant to well-recognized and understood principals, the gate-control theory of pain contemplates that certain cutaneous stimuli can act to inhibit transmission of small-diameter nociceptive fibers. Specifically, the gate-control theory of pain postulates that the spinal gate is influenced by the relative amount of excitatory activity in afferent, large-diameter nerve fibers versus small-diameter nociceptive fibers that verge in the superficial laminae of the spinal cord dorsal horn (i.e., the substantia gelatinosa). The stimulus produced by the device 20 may thus be appropriately situated to generate activity in neighboring large-diameter nerve fibers situated in the pelvic/genitourinary regions to thus inhibit transmission of nociceptive signals. Specifically, the device 20 will impart a stimulus that will counter-balance the activity of small-diameter fiber excitatory activity to thus partially suppress the level of nociceptive input that reaches the brain. The well-established principals governing the gate-control theory of pain may be found in Warfield, Carol A.: "Expert Pain Management", Springhouse Publishing, Co., pages 141–143, the disclosure which is expressly incorporated herein by reference.

In addition or as an alternative to housing signaling device 20 for imparting the stimuli discussed above, the saddle member 12 may further have disposed therein at least one, and preferably a multiplicity of magnets (not shown) that are configured and oriented to impart magnetic therapy to the pelvic genitourinary regions of the body. In this regard, such magnets will be oriented such that the north or negative poles thereof are oriented to become situation in close proximity with the user's pelvic/genitourinary regions as per conventional magnetic therapy. With respect for use in the present application, it is contemplated that any conventional magnets, including ceramic, neodymium and/or plastalloy may be utilized. Moreover, it is readily recognized and appreciated by those skilled in the art that any or a variety of magnets having different dimensions and geometric configurations may be utilized in the practice of the present invention.

Advantageously, by so positioning such magnets within the saddle member 12, the user may thus receive the benefit of experiencing magnetic therapy, particularly with respect to the organs and anatomic structures in the pelvic/genitourinary region, including, but not limited to, the small and large intestines, rectum, lower urinary tract, sexual/reproductive organs, hip/lower back and other neighboring joints and bones. Such magnetic therapy will further be imparted to the pelvic muscles, such as the levator ani and obturator internus, and the muscles adjacent to the pelvis, such as the adductor longus, as discussed above.

Figure 5:
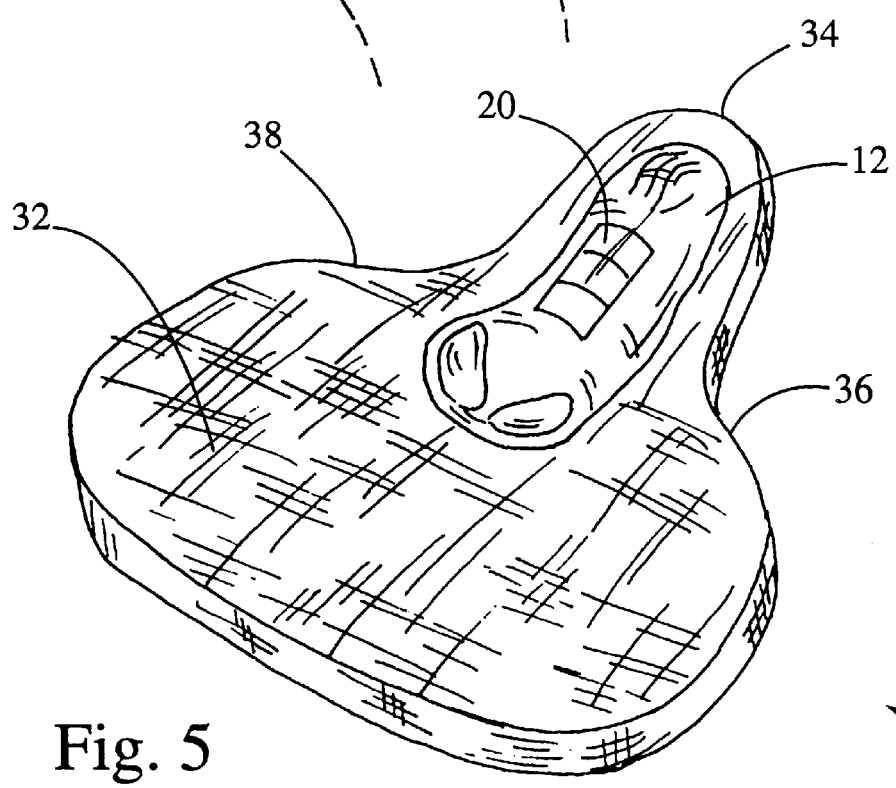
FIG. 5 is a perspective view of the external exercise device of the present invention as formed within a conventional seat cushion.

Referring now to FIG. 5, there is shown the external exercise device of the present invention as disposed within a conventional seat member or cushion 30. Such seat cushion 30, which may take the form of a variety of designs well-known to those skilled in the art, is preferably provided with a generally planar area 32 to accommodate to the buttocks of the individual seated thereupon, and a protruding portion 34 flanked by recesses 36, 38 which thus defines an area upon which the individual may straddle. As illustrated, disposed within such portion 34 is the exercise device 10 with the signaling device 20 thereof being upwardly oriented and configured to aligned with and compress through the seat and against the crotch of the individual seated upon the seat member 30.

When an individual is seated thereupon, the device 10 of the of the present invention may be utilized to impart the necessary stimulus to the individual to thus identify the target muscle groups of the pelvic floor and remind the person to perform the pelvic muscle strengthening exercises therefor at predetermined times. As discussed above, the stimulus produced by the signaling device 20 may take the form of vibration, heat, and/or pressure. However, in the embodiment shown, it will be understood and appreciated that the stimulus produced by the signaling device 20 will be necessarily of a sufficient degree so as to be perceived by the individual seated upon the seat cushion 30, and more particularly the predetermined region of the person's anatomy resting thereupon (i.e, the crotch) to remind the user to perform the pelvic muscle strengthening exercises. Additionally, as per the aforementioned discussion, the signaling device 20 may be modified to impart a desired degree of stimulation to the sexual organs to thus impart a pleasurable experience. Likewise, such device 10, and more particularly the saddle member 12 thereof, may be embedded with one or more magnet members to thus impart magnetic therapy to the individual sitting upon such seat cushion.

As will be appreciated by those skilled in the art, by incorporating the novel exercise device 10 of the present invention into such conventional seating devices 30 can thus eliminate the need to directly compress or otherwise mount the device 10 of the present invention directly upon the crotch or pelvic region of the user. Advantageously, such design enables those individuals in need of a strengthening exercise regimen to be provided with the necessary stimulus to adhere to such regimen, while simply remaining seated and thus free to do normal activities, such as work and the like.

It is to be understood that the individual elements and components of each above-described embodiment may be interchanged among and/or incorporated into any and all embodiments of the invention, even though certain elements or components may have been mentioned or described herein with respect certain embodiment(s) of the invention only.

It is to be further understood that various additions, deletions, modifications and alterations may be made to the above-described embodiments without departing from the intended spirit and scope of the present invention. Accordingly, it is intended that all such additions, deletions, modifications and alterations be included within the scope of the following claims.

What is claimed is:

1. A device for reminding a patient to perform pelvic muscle strengthening exercises comprising:
    a) a saddle member adapted to be positioned upon the pelvis of said patient; and
    b) a stimulator disposed within said saddle member for imparting a perceptible stimulus to said patient at predetermined times to remind said patient to perform said pelvic muscle strengthening exercises.

2. The device of claim 1, wherein said saddle member comprises an elongate seat portion having an anterior end and a posterior end, said seat portion being designed and configured to be straddled by said patient such that said stimulator compressively engages the sexual organs of said patient and imparts a vibratory stimulus thereto.

3. The device of claim 2, wherein said stimulator imparts a stimulus selected from the group consisting of vibration, pressure, heat, and friction to the sexual organs of a male patient straddling said seat portion.

4. The device of claim 2, wherein said stimulator imparts a stimulus selected from the group consisting of vibration, pressure, heat, and friction to the sexual organs of a female patient straddling said seat portion.

5. The device of claim 1 wherein said device further includes:
    c) a timer apparatus disposed within said saddle member and coupled to said stimulator to selectively exert said perceptible stimulus at predetermined times.

6. The device of claim 1 wherein said device is adapted to be disposed within a conventional seat cushion.

7. The device of claim 1 wherein said stimulator is further designated and configured to compressively engage the pelvic floor muscles of said patient responsible for urinary continence and impart said perceptible stimulus thereto.

8. The device of claim 1 wherein said stimulator is further designated and configured to compressively engage the pelvic floor muscles of said patient responsible for fecal continence and impart said perceptible stimulus thereto.

9. The device of claim 1 wherein said stimulator imparts a perceptible stimulus to at least one (1) pelvic muscle selected from the group consisting of levator ani, obturator internus, sphincter, bulbospogeosus buobocavernus, transverse perineal, and ischiocavernus.

10. The device of claim 1 wherein said stimulator imparts a perceptible stimulus to at least one (1) muscle adjacent to the pelvis selected from the group consisting of adductor longus, external hip rotators, and the gluteal.

11. A method for reminding a patient to perform pelvic muscle strengthening exercises comprising the steps:
    a) providing a saddle member adapted to be positioned upon the pelvis of said patient, said saddle member having a signaling device disposed therein for imparting a perceptible stimulus to said patient;
    b) compressively engaging said saddle member against the pelvic floor muscles of said patient responsible for urinary incontinence; and
    c) periodically activating said signalling device at predetermined times such that said patient is caused to perceive such stimulus produced by said signalling device and perform said pelvic muscle strengthening exercises.

12. The method of claim 11 wherein in step a), said signalling device comprises a vibrator.

13. A pain management apparatus for the treatment and control of pain experienced by a patient comprising:
    a) a saddle member adapted to be positioned upon the pelvis of said patient;
    b) a stimulator disposed within said saddle member for imparting a perceptible cutaneous stimulus to said patient at predetermined times; and
    c) wherein said cutaneous stimuli is of sufficient magnitude to suppress a flow nociceptive neuroactivity from the patient's peripheral nerve fibers to said patient's spinal cord to thereby reduce the pain perceived by the patient.

14. The method of claim 13 wherein in step b), said stimulus is selectively imparted to large-diameter afferent nerve fibers.

15. The device of claim 1 wherein said saddle member further includes at least one protuberance formed thereon for imparting acupressure therapy to the pelvic region of the patient when said patient straddles said saddle member.

16. A method for the management of pain in a patient comprising the steps:
   a) providing a saddle member adapted to be positioned upon the pelvis of said patient, said saddle member having a stimulator disposed therewithin for imparting a perceptible cutaneous stimulus to said patient, said cutaneous stimuli being of sufficient magnitude to suppress a flow of nociceptive neural activity from the patient's peripheral nerve fibers to said patient's spinal cord to thereby reduce the pain perceived by the patient;
   b) compressively engaging said saddle member against the pelvis of said patient; and
   c) periodically activating said stimulator such that said patient is caused to perceive said cutaneous stimuli produced from said stimulator.

* * * * *